United States Patent
Schaaf et al.

(10) Patent No.: US 6,764,439 B2
(45) Date of Patent: Jul. 20, 2004

(54) DEVICE FOR IMPROVING DRAINAGE OF THE AQUEOUS HUMOR WITHIN THE EYE OF A LIVING BEING

(75) Inventors: Hansgeorg Schaaf, Reichertshausen (DE); Robert Stegmann, Pretoria (ZA); Werner Maag, Glarus (CH)

(73) Assignee: Grieshaber & Co. AG Schaffhausen, Schaffhausen (CH)

( * ) Notice: Subject to any disclaimer, the term of this patent is extended or adjusted under 35 U.S.C. 154(b) by 0 days.

(21) Appl. No.: 09/902,850

(22) Filed: Jul. 11, 2001

(65) Prior Publication Data

US 2001/0053873 A1 Dec. 20, 2001

Related U.S. Application Data

(63) Continuation of application No. PCT/CH00/00627, filed on Nov. 23, 2000.

(30) Foreign Application Priority Data

| Nov. 24, 1999 | (DE) | ......................................... 199 56 517 |
| Nov. 24, 1999 | (DE) | ......................................... 199 56 515 |
| Oct. 20, 2000 | (CH) | ..................................... 2000 2055/00 |

(51) Int. Cl.$^7$ ............................................... A61B 1/018
(52) U.S. Cl. ....................................... 600/106; 600/104
(58) Field of Search ................................ 600/104, 105, 600/106, 109, 138, 153, 160, 167; 606/169, 171

(56) References Cited

U.S. PATENT DOCUMENTS

| 4,607,622 | A |   | 8/1986 | Fritch et al. |
| 4,854,302 | A | * | 8/1989 | Allred, III ................... 600/109 |
| 5,275,607 | A | * | 1/1994 | Lo et al. ..................... 606/169 |
| 5,480,409 | A | * | 1/1996 | Riza .......................... 606/205 |
| 5,651,783 | A |   | 7/1997 | Reynard |
| 6,221,007 | B1 | * | 4/2001 | Green ........................ 600/160 |

FOREIGN PATENT DOCUMENTS

| DE | 195 42 955 A | 5/1997 |
| EP | 0 316 244 A | 5/1989 |
| EP | 0 550 791 A | 2/1992 |

* cited by examiner

Primary Examiner—John P. Leubecker
(74) Attorney, Agent, or Firm—Henry M. Feiereisen; Ursula B. Day

(57) ABSTRACT

A device is disclosed for ophthalmologic microsurgery for improving the drainage of the aqueous humor in the eye of a living being, wherein the device has an endoscope connected to a monitor screen and includes a tube-shaped probe adapted for insertion into an eye, and one or more channels co-axially disposed therein and provided with optical elements for focusing and transmitting images from the viewing field in the eye, and wherein the probe houses a surgical tool which is movable in axial direction and about the longitudinal axis so that by means of the oscillating and/or vibrating tool a passageway can be opened in the tissue of the trabecular meshwork for connecting the anterior chamber with the Schlemm's canal.

39 Claims, 7 Drawing Sheets

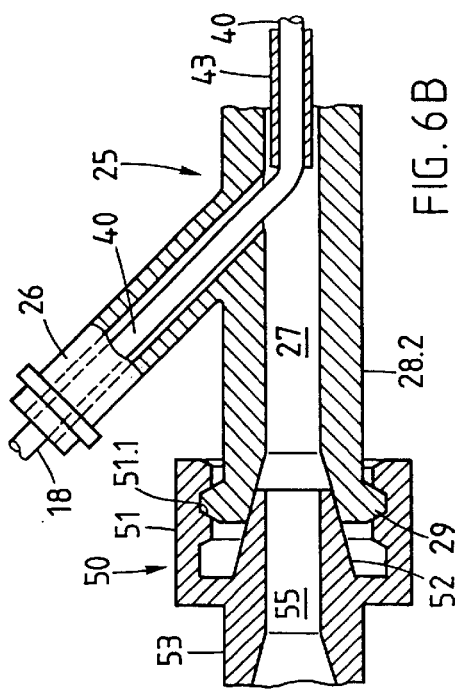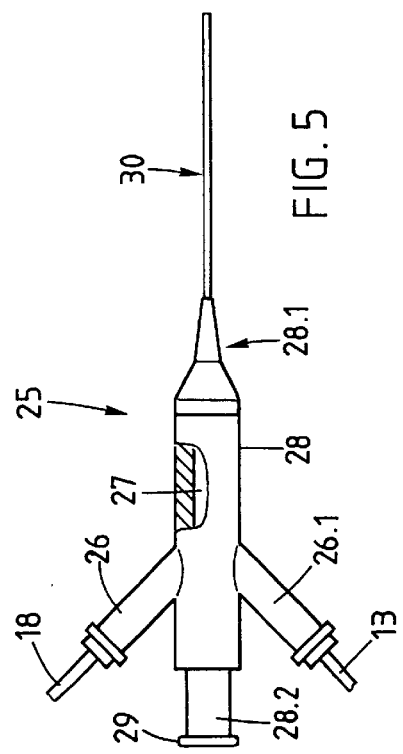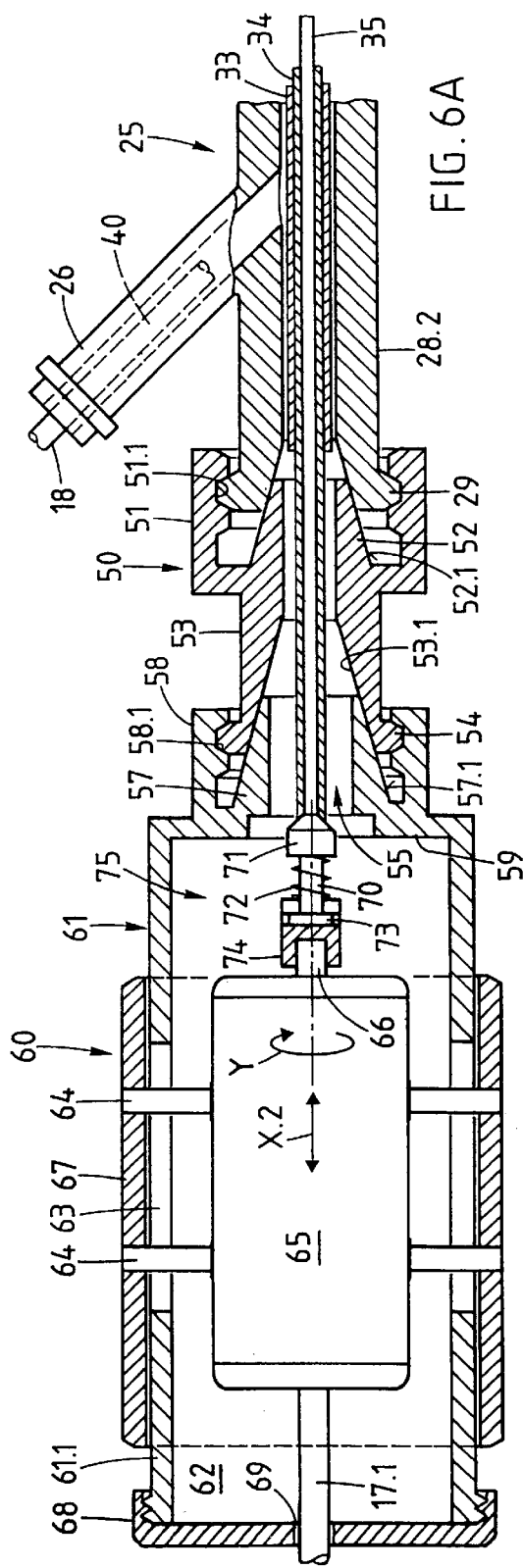

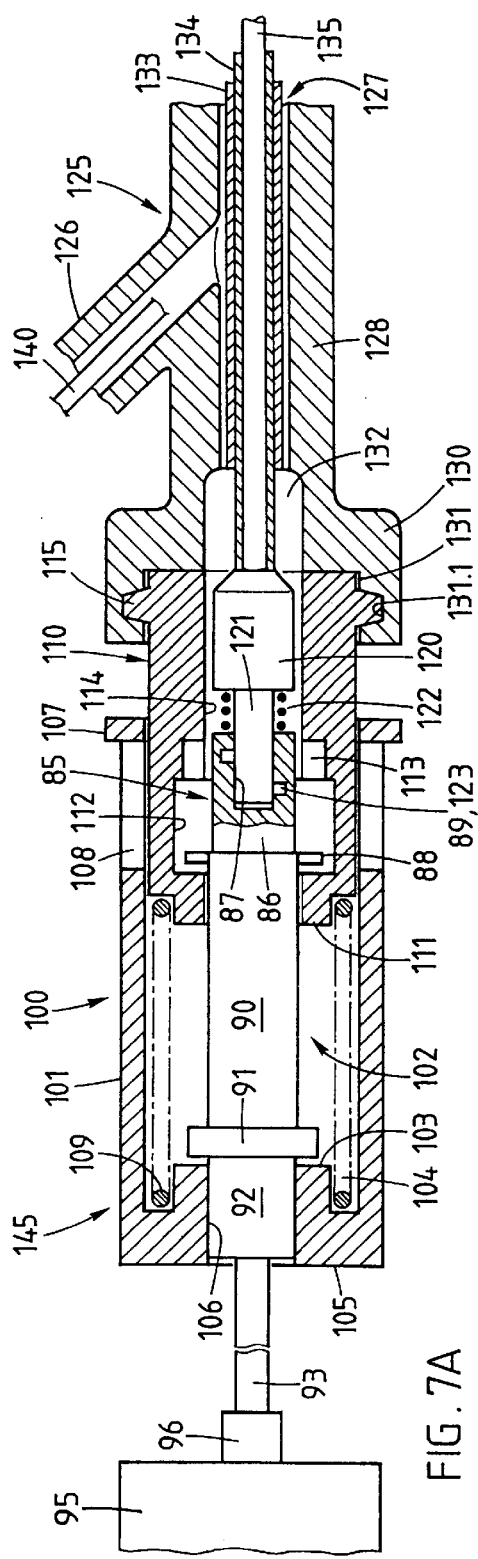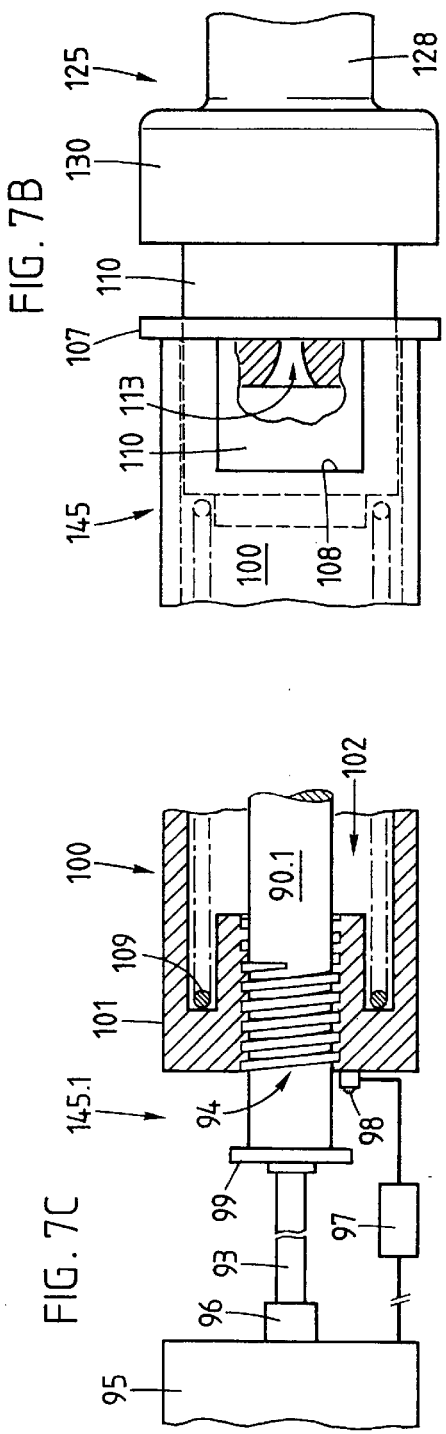
FIG. 7A
FIG. 7B
FIG. 7C

DEVICE FOR IMPROVING DRAINAGE OF THE AQUEOUS HUMOR WITHIN THE EYE OF A LIVING BEING

CROSS-REFERENCES TO RELATED APPLICATIONS

This application is a continuation of prior filed copending PCT International application no. PCT/CH00/00627, filed Nov. 23, 2000.

This application claims the priority of German Patent Applications Serial No. 199 56 515.5, filed Nov. 24, 1999; and No. 199 56 517.1, filed Nov. 24, 1999; and of Swiss Patent Application Serial No. CH 2000 2055/00, filed Oct. 20, 2000, the subject matter of which is incorporated herein by reference.

BACKGROUND OF THE INVENTION

The present invention relates to a device for carrying out ophthalmologic surgical procedures, in particular a device for improving drainage of the aqueous humor in an eye, wherein the secreted aqueous humor in the region of the iridocorneal angle of the anterior chamber is conducted via the trabecular meshwork into the Schlemm's canal and from there through the natural channel system.

The functional capacity of an eye depends on the intraocular pressure (IOP) and requires that the influx and outflow of the aqueous humor (humor aqueous) which circulates between the posterior and the anterior chamber and thereby continually regenerates, is at an equilibrium and natural drainage of the aqueous humor is realized by the aqueous humor flowing at the iridocorneal angle (angulus iridocornealis) via the trabecular meshwork (trabeculum corneasclerale) into the Schlemm's canal and from there via the natural channel system comprising collecting canaliculi and aqueous humor veins.

When changes in the trabecular meshwork occur due to disease or injury, drainage of the aqueous humor is often diminished resulting in a rise of pressure in the eye commonly known as the disease glaucoma that oftentimes leads to visual impairment that can lead to blindness.

From EP-A 0 550 791 a device is known for treatment of the trabecular meshwork concerning changes that lead to obstruction of the aqueous humor drainage induced by disease—and injury. The device is for injecting a suitable medium into Schlemm's canal, which has been partially exposed by cutting open the sclera and folding it upwards. Through this procedure, the venous network of the trabecular meshwork is being stretched and opened at several points effecting a pressure compensation that permits to restore the natural drainage of the aqueous humor by way of the openings, and whereby occlusion of the opening walls is substantially prevented when the walls of the opening are wetted (layered) with the highly viscous medium.

The device and method described in the afore-mentioned printed reference which is directed to the hydraulic stretching of the Schlemm's canal and the resultant bursting of the trabecular meshwork while proven useful, has in practice however shown to be not entirely successful, in particular, opening or stretching of the trabecular meshwork by hydraulic means is unsatisfactory or not realizable at all where due to disease, changes in the trabecular meshwork in the form of clogs and/or occlusions from the trabecular meshwork growing together, have occurred.

SUMMARY OF THE INVENTION

It is thus an object of the present invention to provide an improved device for improving the drainage of the aqueous humor within the eye of a living being, obviating the afore-stated drawbacks. In particular, it is an object of the present invention to provide an improved device for carrying out microsurgery, in particular, for cases where the trabecular meshwork is extremely clogged or has grown together, ophthalmologic surgery can be carried out by which the regulation of the intra-ocular circulation of the aqueous humor may be reactivated and based thereon substantially natural drainage via the trabecular meshwork into the Schlemm's canal is realized.

This object and others which will become apparent hereinafter, are attained in accordance with the present invention by providing a tube-shaped probe for positioning in the anterior chamber in the direction of the trabecular meshwork which is operatively connected to an endoscope. Axially oriented within the probe is at least one tube-shaped working channel and a tube-shaped optical channel comprising at least one optical element for focusing on a viewing field and for transmitting images from a viewing field. An adjustable microsurgical tool which may be driven manually or by electric motor is disposed within the working channel in axial direction relative to the distal end of the tube-shaped probe. By means of the microsurgical tool at least one passageway can be made in the tissue of the trabecular meshwork such that a connection from the anterior chamber to Schlemm's canal is realized and to thereby provide drainage of the aqueous humor via the trabecular meshwork into the Schlemm's canal.

BRIEF DESCRIPTION OF THE DRAWING

The above and other objects, features and advantages of the present invention will be more readily apparent upon reading the following description of a preferred exemplified embodiment of the invention with reference to the accompanying drawing, in which:

FIG. 5 is a schematic representation of an endoscope for the device according to FIG. 1 with a probe disposed thereat;

FIG. 6A is a sectional view on an enlarged scale of a first embodiment of a drive mechanism for the surgical tool disposed in the probe;

FIG. 6B is a partial view of the endoscope according to 6A with a connection piece disposed thereon for connecting a camera to the device according to FIG. 1;

FIG. 7A is a sectional view on an enlarged scale of a second embodiment of the drive of a surgical tool disposed in the probe;

FIG. 7B is a top view of a section of the drive mechanism according to FIG. 7A;

FIG. 7C is a variation of the drive mechanism according to FIG. 7A for the surgical tool disposed in the probe;

DETAILED DESCRIPTION OF PREFERRED EMBODIMENTS

Figure 1:
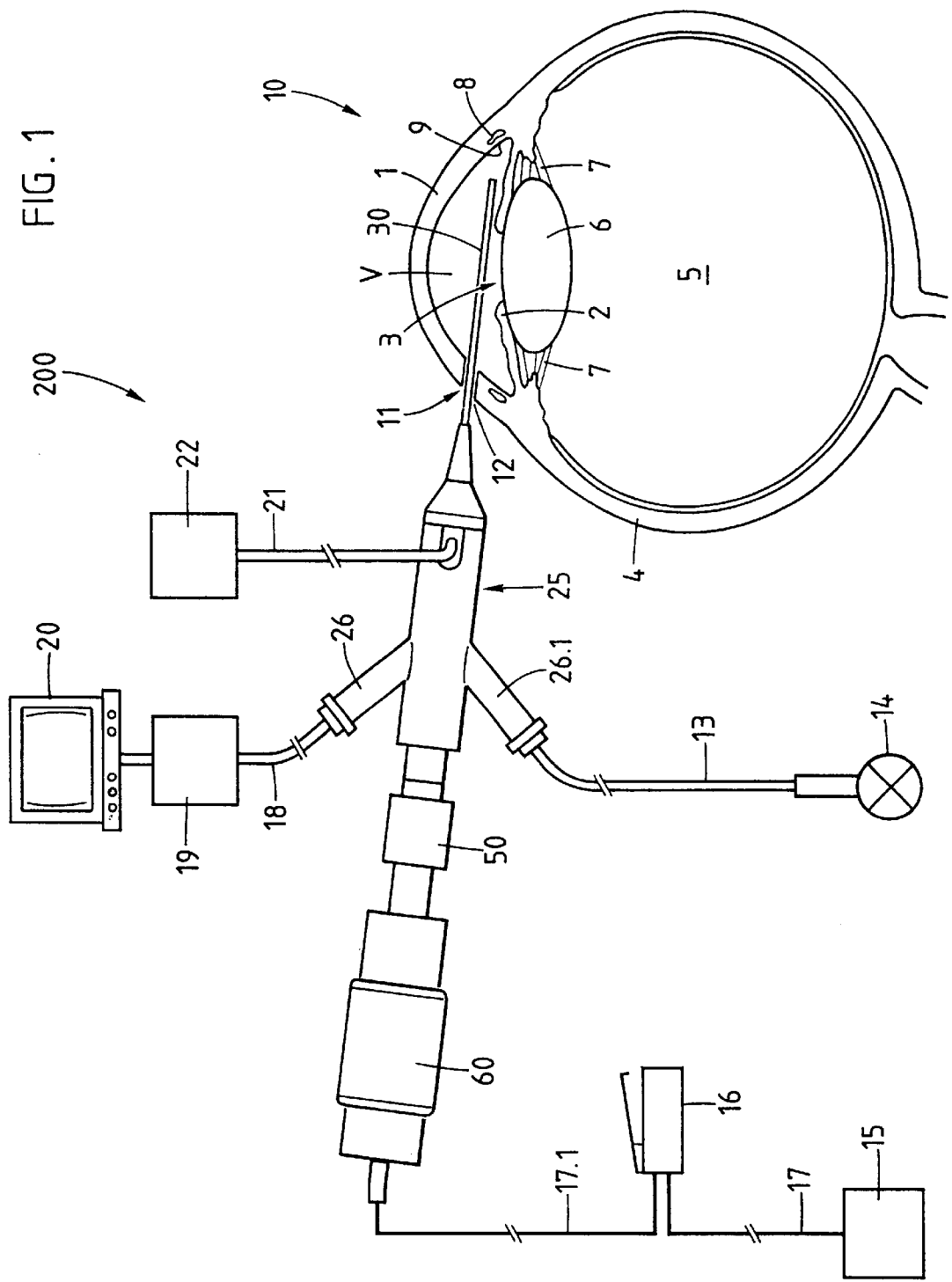
FIG. 1 is a schematic illustration of a device with an endoscope and a probe for carrying out microsurgery on an eye.

Throughout all the Figures, same or corresponding elements are generally indicated by same reference numerals.

Turning now to the drawing, and in particular to FIG. 1, there is shown a schematic representation of the device generally referenced as 200 and comprising a number of functional elements for carrying out microsurgery in an eye of a living being.

To illustrate the invention, an eye 10 is shown in FIG. 1, on an enlarged scale as a section along the longitudinal axis where the cornea 1 is shown, the iris 2, the pupil 3, the sclera 4, the vitreous humor 5, the lens 6 with zonular fibers 7 and the circular Schlemm's canal 8 (sinus venosus sclerae) with the trabecular meshwork 9 in front. In order to insert the probe 30, which is configured as a hollow needle, into the anterior chamber V, an opening 12 (incision) is cut by the ophthalmologist into the cornea in the region of the limbus 11 by means of a suitable surgical instrument, for example a knife or like (not shown here). The slit-like opening 12 for insertion of the surgical instrument is approximately 1.5 mm to 2.0 mm wide.

The apparatus 200 shown schematically in FIG. 1 comprises a tube-shaped probe 30 and an endoscope 25 with at least one connection piece 26. The endoscope 25 is connected to a camera 19 via a line 18, which is coupled to the connecting piece 26; and the camera is connected to a monitor screen 20. Within the tube-shaped probe 30, optical elements are disposed by means of which, images from the viewing field of the iridicorneal angle can be taken with the connected camera 19 and transmitted to the monitor 20 for viewing. The tube-shaped probe 30 is disposed with either a single optical element or with two optical elements arranged relative to each other and connected to the camera 19 in such a manner, that the viewing field for the surgery is generated either as a monoscopic or stereoscopic (three-dimensional) image onto the monitor 20 where it is accordingly on view for the ophthalmologist.

The endoscope 25, schematically represented in FIG. 1 is connected to a drive mechanism 60 by means of a housing-shaped coupling member 50. The drive mechanism 60 is at the one hand, operatively connected to the tube-shaped probe 30 and the mechanical functional elements for carrying out the microsurgery, and on the other hand, via a line, operatively connected to an energy source.

In the embodiment as depicted, the drive mechanism 60 is operatively connected with an electric energy source 15 via an electric line 17 and 17.1 with a switch arranged therebetween. The switch of the drive mechanism 60 is activated, for example, by means of a foot pedal 16. In a variation, not shown here, the functional elements may be activated by an electric current supply (battery) which is connected to the drive mechanism 60 or which is disposed within the housing of the drive mechanism 60.

In a first embodiment, the endoscope 25 as schematically represented in FIG. 1, has a second connection piece 26.1 which is connected in the interior space 27 (FIG. 5) of the endoscope 25 to which a fiber light guide 13 connected to a light source 14 is connected. The light guide 13 penetrates the endoscope in a manner not shown here in detail and is disposed in an auxiliary channel axially oriented in the tube-shaped probe 30. FIGS. 3D and 3G depicts the channel for the light guide disposed in the tube-shaped probe 30.

In a second embodiment, the endoscope 25 is coupled, via a line 21, to an aspiration—and irrigation unit 22 shown in schematic representation. The line 21 penetrates the endoscope 25 in a manner not shown here and is likewise disposed in an auxiliary channel, which is axially oriented in the tube-shaped probe 30. In FIGS. 3D and 3G, the channel within the tube-shaped endoscope 30 for the line 21 is shown.

Figure 2:
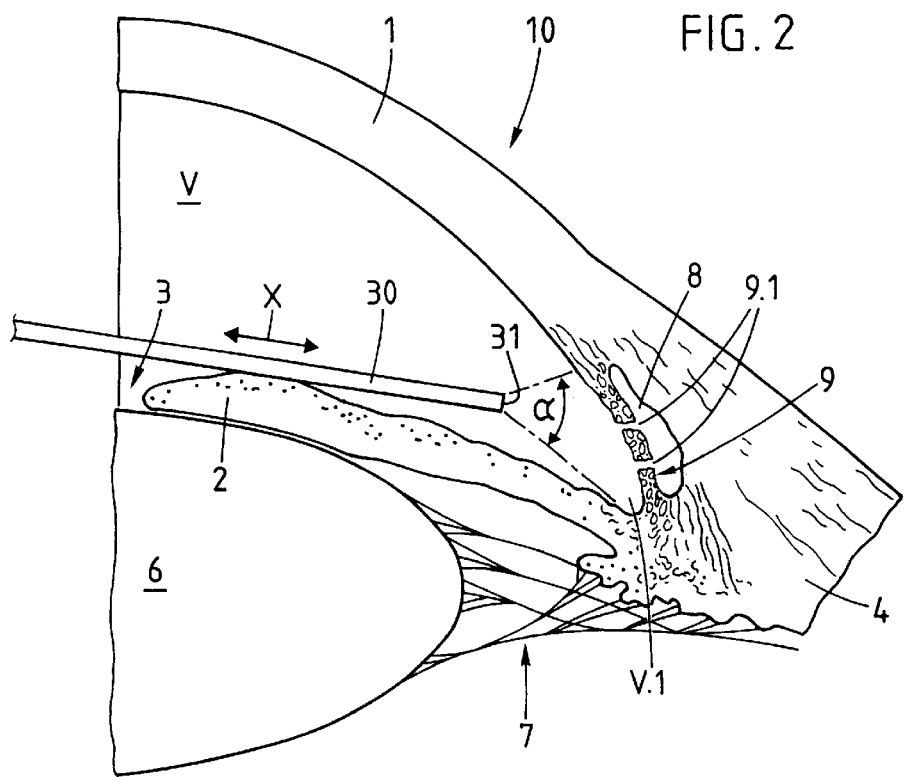
FIG. 2 is a sectional view of a part of an eye on an enlarged scale showing a probe inserted into the anterior chamber.

FIG. 2 depicts a section of the eye 10 on an enlarged scale with the cornea 1, the iris 2, the lens 6, the zonular fibers 7, the sclera 4 as well as Schlemm's canal 8 and the trabecular meshwork which is located anteriorly thereto. Depicted further in FIG. 2 is a portion of the tube-shaped probe 30 attached to the endoscope 25 (FIG. 1), which is shown inserted and directed towards the iridicorneal angle V.1. The probe 30 is axially movable together with the endoscope 25 in the direction of the double arrow X. Through suitable movement, the probe 30 with its distal end 31 is focused relative to the trabecular meshwork 9, thereby realizing a possibly large viewing field by means of the optical functional elements of the probe 30.

The spatial—or opening angle α for the viewing area as seen in FIG. 2 in form of a path of rays is preferably in the range of about 120°.

Suitable configurations of the tube-shaped probe and the likewise tube-shaped channels received therein for holding the mechanical and functional elements are described herein. Each of the probes 30, respectively 30.3, as depicted in FIGS. 3A, 3B and 3E are configured for the monoscopic transmission of images and the probes 30.1 and 30.2 as depicted in FIGS. 3C and 3D as well as probes 30.4 and 30.5 as depicted in FIGS. 3F and 3G are configured for the stereoscopic transmission of images.

Figure 3A:
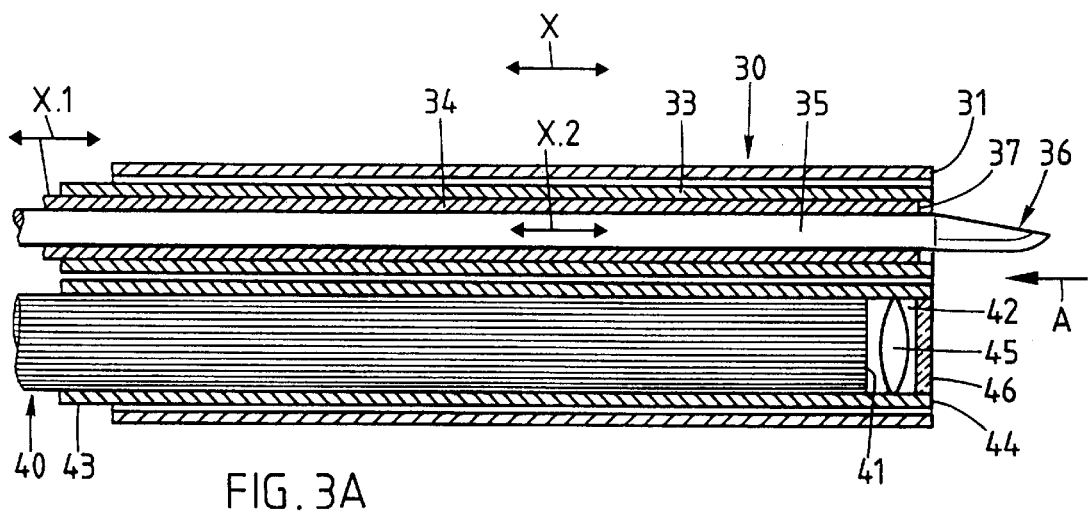
FIG. 3A is a sectional top view of a part of the probe configured in the shape of a hollow needle and having an optical channel and a working channel.
Figure 3B:
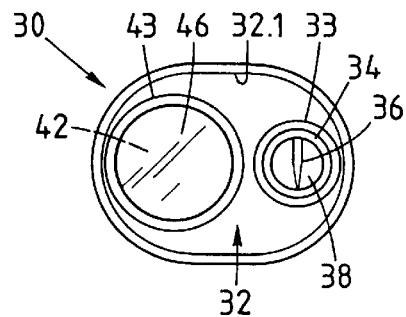
FIG. 3B is a view of the probe in the direction of arrow A according to FIG. 3A showing the optical channel and disposed opposite thereto the working channel.
Figure 3C:
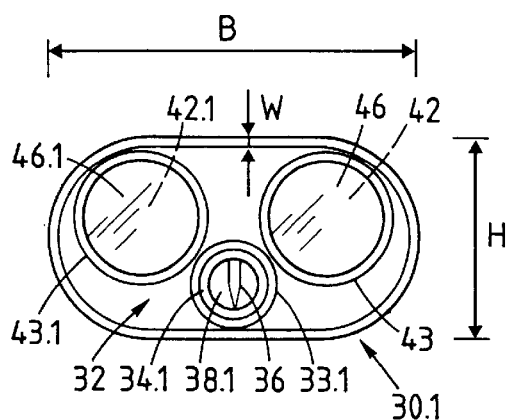
FIG. 3C is a view of a first variation of the probe having two optical channels and a working channel arranged therebetween.
Figure 3D:
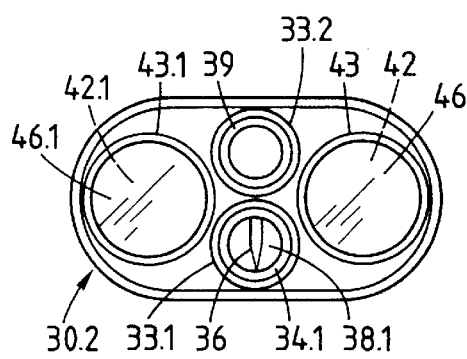
FIG. 3D is a view of a second variation of the probe having two optical channels and two working channels arranged therebetween.
Figure 3E:
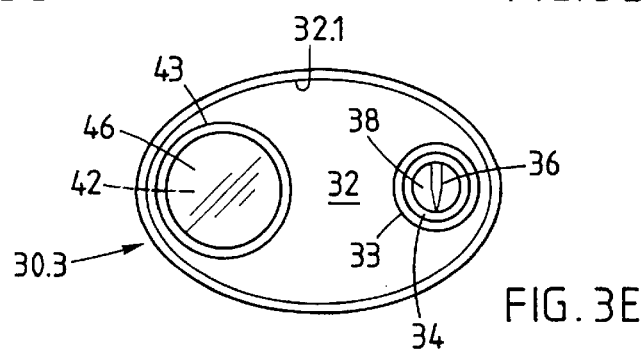
FIG. 3E is a view of a second embodiment of the probe having one optical channel and a working channel arranged opposite thereto.
Figure 3G:
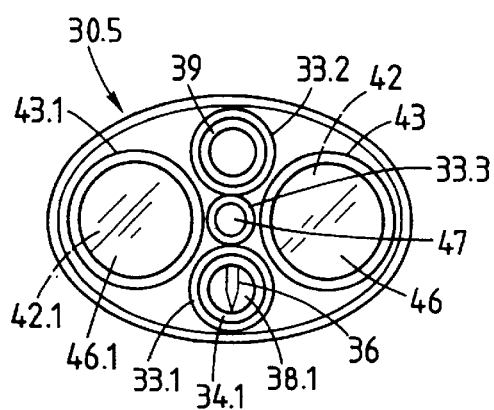
FIG. 3G is a view of a second variation of the probe according to FIG. 3E with two optical channels and working channels arranged therebetween.
Figure 3F:
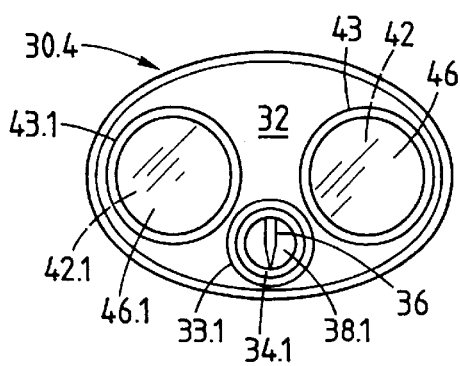
FIG. 3F is a view of a first variation of the probe in FIG. 3E with two optical channels and a working channel arranged therebetween.

FIG. 3A, is a sectional view on an enlarged scale of a first embodiment of the probe 30 showing the axially oriented working channel 33 therein and parallel thereto and at a distance, the optical channel 43. A guide tube 34 and a surgical tool 35 shown schematically here, are disposed in working channel 33. At the distal end of the surgical tool 35 a head piece is provided, which is configured as a working tool such as for example a knife, as seen in FIG. 3A. In further variations, the headpiece 36 is essentially configured as a cutting—grasping or clamping tool or like, as described below.

Guide tube 34 is movable in the direction X.1 of the double arrow relative to the working channel 33 disposed stationary in probe 30, or relative to the distal end 31 of probe 30 and movable in axial direction. Furthermore, the surgical tool 35 is axially movable relative to the distal end 37 of guide tube 34 or relative to the distal end 31 of probe 30 in the direction of the double arrow X.2. The various motions carried out with the headpiece 36 of the surgical tool 35 and effected by the drive mechanism which is actuatable either manually or by electric motor, are also described in further detail below.

The optical channel 43 (FIG. 3A) attached within the probe 30 by means not shown here, comprises an optical guide 40 disposed therein for monoscopic image transmission. An optical lens 45 is disposed within an interior space 42 of channel 43 and between the distal end 41 of the optical guide 40 and the distal end 44 of the tube-shaped optical channel 43. The distal end 44 of the tube-shaped optical channel 43 is preferably sealed off by means of a transparent (translucent) disc 46 or like. The optical guide 40 consists for example of a plurality of bundled optical light guide fibers.

FIG. 3B depicts a front view of a cross section of probe 30 in the direction of arrow A according to FIG. 3A and wherein the probe is configured as a flat oval hollow needle and wherein the tube-shaped working channel 33 and the tube-shaped optical channel positioned opposite thereof are disposed in the interior space 32 of the probe 30. The working channel 33 and the optical channel 43 are preferably attached to the wall 32.1 of the probe 30 by means not shown here. Disposed in the interior space (not further identified) of the working channel is the guide tube 34 with interior space 38 and configured for receiving the head piece 36 of the surgical tool as depicted in a schematic representation in FIG. 3B. The optical channel 43 has an interior space 42 for receiving the afore-referenced optical elements 40, 45, 46 as depicted in FIG. 3A, whereby FIG. 3B depicts the translucent disc 46 in schematic representation.

In FIG. 3C, a first variation of the probe 30.1 is shown in a plan view configured as a flat-oval hollow needle. As compared to the embodiment as shown in FIG. 3B, the probe 30.1 with interior space 32, comprises two optical channels 43 and 43.1 that are diametrically arranged in the interior space 32 at a distance from each other, and set-off thereto, a working channel 33.1 disposed between the two optical channels. Disposed in the interior space of the working channel (not referenced) is the guide tube 34.1 having an interior space 38.1 like in FIG. 3B and configured for receiving the head piece 36 which is seen here in a schematic representation. Both, channels 43 and 43.1 with their respective interior spaces 42 and 42.1 are configured for receiving optical element 40, 45, and 46 as afore-described in reference to FIG. 3A, wherein the two translucent discs 46 and 46.1 are schematically represented in FIG. 3C.

FIG. 3D shows the second variation of the probe referenced as 30.2 and configured as an oval hollow needle. The probe 30.2 is configured like the afore-described variation in FIG. 3C and comprises the two optical channels 43 and 43.1 that are diametrically disposed at a distance from each other. In a variation from the embodiment as depicted in FIG. 3C, the present variation is configured with a second working channel 33.2 and corresponding to the first working channel 33. In the second working channel 33.2, a line 39 is provided, which is coupled to the aspiration—and irrigation unit 22 via line 21 (FIG. 1) in a manner not shown here.

FIGS. 3E, 3F and 3G respectively depict a plan view of a second embodiment of the probe 30.3, 30.4 and 30.5 configured as a hollow needle. In a variation from the embodiment according to FIGS. 3B and 3C and 3D, the probes 30.3 and 30.4 and 30.5 according to section views in FIGS. 3F to 3G are each configured as an elliptical hollow needle. The channels with the functional element arranged therein and disposed in the respective probes 30.3, 30.4 and 30.5 (FIGS. 3E to 3G) are configured essentially like the afore-described channels shown in connection with FIGS. 3B to 3D. Preferably, the interior assembly of FIG. 3E like the assembly according to FIG. 3B, and the interior assembly of FIG. 3F are approximately like the assembly according to FIG. 3C and the interior assembly of FIG. 3G is configured substantially according to the assembly as in FIG. 3D.

The probes 30 to 30.5 as schematically represented on an enlarged scale in FIGS. 3B to 3G in a cross sectional view along a flat-oval or elliptical vertical axis have a height H of about 1.25 mm, a width B of about 2.41 mm and a wall thickness W of about 0.08 mm.

It should be noted, that the embodiments of the probes 30 to 30.3 as depicted in FIGS. 3B and 3E, are each configured with the optical channel 43 disposed therein for the monoscopic transmission of images. The embodiments of probes 30.1 and 30.2 and 30.4 and 30.5 as depicted in FIGS. 3C and 3D and FIGS. 3F and 3G each have disposed therein optical channels 43 and 43.1 configured for the stereoscopic (three-dimensional) transmission of images.

In a further variation depicted in FIG. 3G, an additional channel 33.3 is located between the channels 43 and 43.1, respectively channels 33.1 and 33.2. The channel 33.3 is configured for receiving a light guide 47 shown here in schematic representation. The light guide 47 disposed in the channel 33.3 serves for the emission of a bundle of light rays to suitable illuminate the area for surgery in the iridocorneal angle V.1 (FIG. 2).

At the distal end of each of the surgical tools situated in the working channel, respectively in the guide tube of each of the probes 30, 30.1, 30.2, 30.3, 30.4, or 30.5 a headpiece is provided, which is configured for carrying out microsurgery. The headpiece of the surgical tool is configured as an elongated tool or wire and is operatively coupled to a drive mechanism. Due to the relatively flexible and spongy consistency of the tissue of the trabecular meshwork 9 (FIG. 2), the surgical tool with the headpiece is configured in the shape of, for example a knife, a gripping—or clamping element (forceps), scissors, or in the shape of a cylindrical cutting element, a cylindrical router, or a drill or like.

Embodiments of the headpiece, which can either be attached to the respective surgical tool or is integral to the tool are described in the following paragraphs in connection with the FIGS. 4A to 4K. For purposes of simplifying the description that follows, each of the variations shown in an enlarged scale relate to the distal end of the probe not shown in FIGS. 3A to 4K.

Figure 4A:
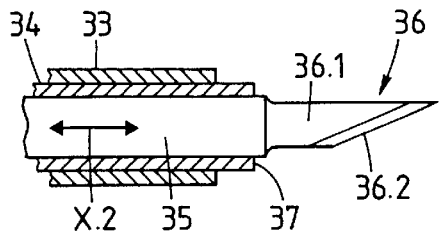
FIG. 4A is a sectional view depicting a first embodiment of the working channel having a surgical tool configured as a one-edged knife.

A first embodiment in FIG. 4A shows a sectional view of the distal end of the working channel 33 with the guide tube 34 and the surgical tool 35 co-axially disposed therein. The headpiece 36 which is integrally formed at the distal end of the surgical tool 35 is configured, for example, in the shape of a knife 36.1 having a blade 36.2. In this embodiment, the surgical tool, which is movable to and from an axial direction according to the direction of the double arrow X.2, has a knife 36.1 projecting from the distal end 37 of the guide tube 34 for carrying out the microsurgery respectively for opening a passageway 9.1 into the trabecular meshwork 9 (FIG. 2).

Figure 4B:
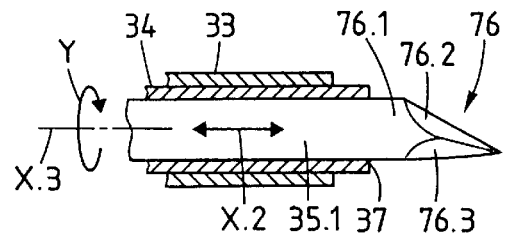
FIG. 4B depicts the surgical tool according to FIG. 4A configured as a double-edged knife.

A variation of the first embodiment according to FIG. 4A is shown in FIG. 4B where the headpiece 76 at the surgical tool is configured as a knife 76.1. In a variation of the embodiment as shown in FIG. 4A, the knife 76.1, is configured with blades 76.2 and 76.3. In this variation of the embodiment, the surgical tool 35.1 with the head piece 76 projecting from the distal end is rotatably driven about its rotational axis X.3 according to the direction of arrow Y. In a further variation the rotatably drivable surgical tool 35.1 is additionally movable in axial direction along double arrow X.2.

Figure 4C:
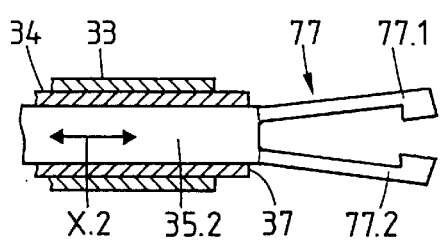
FIG. 4C is a sectional view of a second embodiment of the working channel with a surgical tool disposed therein which is configured as a clamping element (forceps)

FIG. 4C depicts a sectional view of a second embodiment of the distal end of the working channel 33, with the guide tube 34 and the surgical tool 35.2 disposed co-axially therein. The surgical tool 35.2 is provided with a headpiece 77, configured with two spread-apart clamping arms 77.1 and 77.2. In order to realize the clamping function required for the microsurgery, both clamping arms are pressed together, for example, by a relative motion of the guide tube 34 along axial direction X.2 with respect to the proximal end of the head piece 77, whereby by means of a small culling motion, relatively small tissue particles of the spongy tissue of the trabecular meshwork 9 can be grasped and removed for forming each passageway 9.1 (FIG. 2).

Figure 4D:
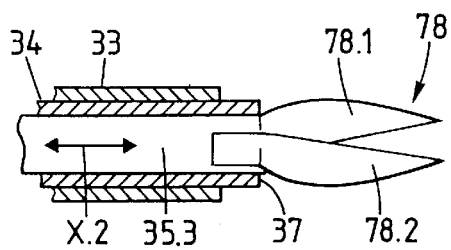
FIG. 4D is a sectional view of a third embodiment of the working channel with a surgical tool disposed therein which is configured as scissors.

FIG. 4D is a sectional view of a third embodiment showing the distal end 37 of working channel 33 with guide tube 34 and the surgical tool 35.3 co-axially disposed therein. The surgical tool 35.3 is provided with a head piece 78 configured as a scissors with two cutting blades that are spring-biased. The cutting function is realized when the two cutting blades 78.1 and 78.2 are pressed together, for example by a relative motion in axial direction X.2 with respect to the proximal end of the head piece 78 and against the restoring force of the spring-biased blades, thereby cutting the spongy tissue of the trabecular meshwork 9 for the formation of a passageway 9.1 (FIG. 2).

Figure 4E:
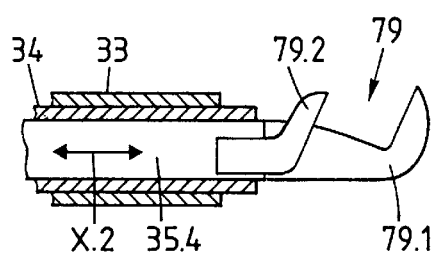
FIG. 4E is sectional view of a variation of the surgical tool configured as scissors with cutting blades axially movable and in open position.
Figure 4F:
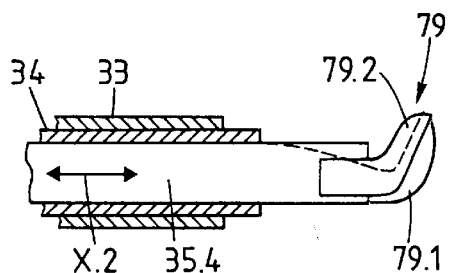
FIG. 4F is a surgical tool configured as a scissors according to FIG. 4E with the cutting blades in closed position.

FIG. 4E and FIG. 4F show a variation of the embodiment according to FIG. 4D where the working channel 33 is seen with guide tube 34 and the surgical tool 35.4 provided with the head piece 79, is co-axially disposed therein. The headpiece 79 comprises a stationary first knife or scissors blade 79.1 as well as a second knife 79.2 or scissors blade movable in and from an axial direction X.2 for performing a cutting function. In FIG. 4E, the two knives or scissors blades 79.1 and 79.2 are shown in an open position and in FIG. 4F, they are shown in a closed position.

Figure 4G:
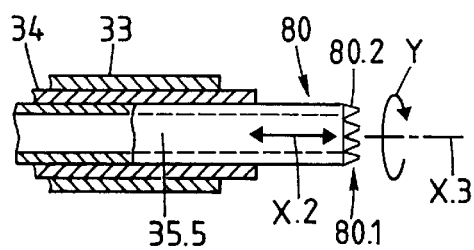
FIG. 4G is a sectional view of a fourth embodiment of the working channel disposed therein with the surgical tool configured as a hollow cylindrical cannula.

FIG. 4G is a partial sectional view of a fourth embodiment showing the distal end of the working channel 33 with the guide tube 34 and the surgical tool 35.5 co-axially disposed therein. The surgical tool 35.5 which is configured in the shape of a hollow cylindrical tube is provided with a head piece 80 having a sawtooth-shaped front face 80.1 and is provided with a conical ground-onto ring surface 80.2, so that the front face exhibits a circular cutting edge 81.1.

Figure 4H:
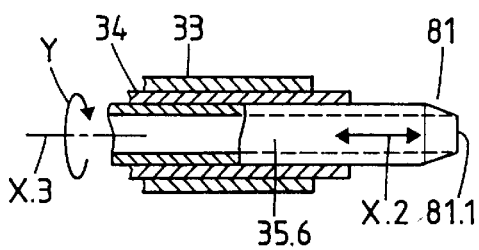
FIG. 4H is a sectional view of a variation of the surgical tool configured as a hollow cylindrical cannula according to FIG. 4G.

The two embodiments as shown in FIG. 4G and FIG. 4H are additionally configured such that the surgically removed tissue particles of the trabecular meshwork 9 can be suctioned off through the hollow cylindrical head piece 80 respectively 81 by other means not shown here.

Figure 4K:
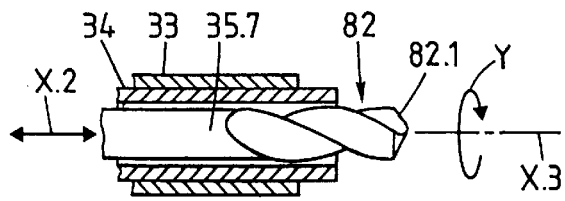
FIG. 4K is a sectional view depicting a further embodiment of the working channel with the surgical tool disposed therein is configured as a drill.

FIG. 4K is a section view of a further embodiment showing the distal end of the working channel 33 with the guide tube 34 and the surgical tool 35.7 co-axially disposed therein. The surgical tool 35.7 is configured in the shape of a drill shown here in a schematic representation, and provided with a headpiece 82 which exhibits at least one cutting edge 82.1. In this variation of the embodiment, the surgical tool 35.7, with the headpiece 80 projecting from the distal end of the guide tube 34, is movable in axial direction along double arrow X.2. and additionally can be rotatably driven about its rotational axis X.3 in the direction of arrow Y.

It should be noted, that the surgical tools, afore-described in connection with FIGS. 4A to 4K, depending on their configuration and means of function of their respective head pieces 36, 76, 77, 78, 79, 80, 81 or 82 are each rotatably axially movable in the direction of double arrow X.2 and/or about their own rotational axis X.3 and direction of arrow X.2 and Y, by means of an electric motor drive mechanism. The afore-described motions and those of each of the surgical tools in direction of the arrow x.2 and Y can also be combined.

Each of the surgical tools 35 and 35.1 to 35.7 may be manually operated by the ophthalmologist, particularly when bringing each of the surgical tools into an axially directed operational position. When using an electric motor drive as the drive mechanism 60, the afore-described motions can be carried out under vibration or oscillation or respectively in combination of both, oscillation and vibration simultaneously.

In another variation, the drive mechanism 60 may be configured as a high frequency generator which is operatively connected to one of the surgical tools for generating ultrasound waves to carry out the microsurgery in the trabecular meshwork 9.

The head pieces 36, 76, 77, 78, 79, 80, 81 of the surgical tools as afore-described are configured in the shape of the knife, the gripping—or clamping element (forceps), the scissors, the cylindrical cutting element, the router or the drill and serve as means for opening a passageway 9.1 in the trabecular meshwork 9, at least at one location preferably at two or more locations, by which passageway a connection of the anterior chamber V with the circular Schlemm's canal 8 in the region of the iridocorneal angle V.1 is realized for drainage of the aqueous humor (FIG. 2). Preferably, during the entire duration of the microsurgery, the tissue particles of the trabecular meshwork that result from the microsurgical cutting are suctioned away by suitable means.

When cutting the passageway 9.1 during the microsurgery, by means of the afore-described surgical tools 35 to 35.7, a highly viscous medium can be injected into the passageway 9.1 by suitable means. The so-wetted surface walls of the passageway 9.1 are preventing local tissue formation (cell proliferation and scar formation) from sealing off the passageway 9.1 cut into the trabecular meshwork 9 (FIG. 2).

FIG. 5 shows a view of the endoscope 25 in a schematic representation where the cylindrical housing 28 with the interior space 27 is shown in a partially cutaway view. At the outer circumference of the housing 28, a first connection piece 26 is disposed for the line 18 and opposite therefrom, the other connection piece 26.1 is disposed for the line 13 (light guide). The two connection pieces 26 and 26.1 are in fluid connection with the interior space 27 of housing 28. At one end, the housing 28 is provided with a first connector 28.1 for the probe 30, which is configured in the shape of a hollow needle. The probe 30 is attached to the connector 28.1 by means not shown here and is likewise in fluid connection with the interior space 27 of the housing 28. At the other end, the housing 28 is provided with a cylindrical part 28.2 and an exterior circular collar 29.

FIG. 6A shows a sectional view of a first embodiment of the drive mechanism 60 on an enlarged scale, which is connected, via the housing-shaped intermediary piece or coupling member 50 to the endoscope 25 shown in partial view. Each of the elements 60 and 50 and 25 are described in the following paragraphs.

The drive mechanism 60 comprises a housing 61 having an interior space 62 and an electric motor 65 disposed therein which is provided at one end with an exit shaft 66. At the other end, the motor drive 65, is in operative connection with the electric energy source as schematically represented in FIG. 1, via the line 17.1. At one end, the housing 61 is sealed by a top, for example a screw-on cap 68 or like. The cap 68 has a bore 69 for the line 17.2. Furthermore, a sliding member 67 which is provided at the outer circumference of housing 61, can be brought into operative engagement with the electric motor 65 by means of catches 64 that are attached to the sliding member and that are guided in corresponding recesses 63 in the housing wall 61.1. At the other end of the housing 61 is an adapter part 58 provided with a snap ring groove 58.1 and an intermediary piece 57 having a conical centering surface 57.1, and which is integrally formed with a front wall 59. The intermediary piece 57, which is circularly surrounded by the adapter part 58 is provided with a through-bore 55 for fluid connection with the interior space 62 of housing 61.

At one end, the housing-shaped coupling member 50 comprises a first housing section 51 which is provided with an inner snap ring groove 51.1 and integrally formed onto housing section 51, is a second housing section 53 having a circular collar 54. The second housing section 53 is provided with a inner conical centering surface 53.1 and the first housing section 51 is provided with an intermediary piece 52 which has an outer conical centering surface 52.1.

At the other end, the housing-shaped coupling member 50 is operatively connected, via the collar 54 disposed within the snap ring groove 58.1, to the drive mechanism 60 by means of the adapter part 58, and also via the circular collar 29 sitting in snap ring groove 51.1 of cylindrical part 28.2 disposed at endoscope 25. Elements 25, 50 and 58, 61 which are provided with conical centering surfaces are, for example, operatively connected into an assembly unit by means of a bayonet catch or snap lock. The interior space as formed by each of elements 25, 50 and 61 is configured for receiving the tube shaped working channel 33 of guide tube 34 with the surgical tool 35 co-axially disposed therein. The guide tube 34 and the wire-shaped surgical tool 35 co-axially disposed therein each are configured for flexibility.

The surgical tool 35, which is configured for example in the form of an elongated wire or like, is in operative connection with the exit shaft 66 of the electric motor 65 via a coupling 75, as schematically represented in FIG. 6A. The coupling 75 comprises a pressure piece 71 which is fastened by means not shown here to the proximal end of the surgical tool 35 which is disposed within the guide tube 34. The side of the pressure piece 71 facing towards the guide tube 34 is provided with a circular abutting surface shown here not in detail. The side of the pressure piece 71 facing away form the guide tube 34 has at its front end a pin-shaped actuator 70 with an attachment piece 73 and disposed thereat by means not shown here. The pin-shaped actuator 70 is disposed with the attachment piece 73 in a correspondingly configured recess of the head piece 74 that is operatively connected to the exit shaft 66 of the electric motor drive 65. A pressure spring 72 is disposed at the actuator 70 between the pressure piece 71 and the headpiece 74.

FIG. 6B depicts a partial sectional view of the endoscope 25 on an enlarged scale and disposed thereon the casing section 51 of the coupling member 50, that is attached to the cylindrical part 28.2 of endoscope 25 by means of collar 29 engaging in the snap ring groove 51.1. Furthermore, the tube-shaped optical channel 43 with the optical guide 40 disposed therein, is shown in the interior space 27 of endoscope 25. Optical guide 40 projects through the connection piece 26 disposed at endoscope 25 and is coupled to line 18 which leads to camera 19 (FIG. 1) in a manner not shown here in detail.

FIG. 7A depicts a sectional view on an enlarged scale of a second embodiment of the drive mechanism 145 disposed at the endoscope 125. The drive mechanism 145 comprises a housing 100, a coupling member 110 as well as a control member 90 disposed in the interior space 102 of housing 100. The control member 90 which is provided with cylindrical core 92 and a stop collar 91 is in operative connection with the exit shaft 96 via drive shaft 93 of the drive mechanism. The two shafts 93 and 96 are connected to each other for disengagement, for example, by means of suitable coupling—or connection elements in a manner not shown here in detail. The drive mechanism 95 with exit shaft 96 is preferably configured as an electric motor drive.

The housing 100 is configured as a cylindrical body 101 with an interior space 102 for receiving the respectively configured functional elements therein. One end of the cylindrical body 101 is provided with a rear wall 105 having a through-bore 106 for supporting the control member that is provided with the cylindrical core. A cylindrical shoulder 103 extends from the rear wall 105 into the interior space 102, thus forming a circular pocket 104, which is configured for receiving and attaching a pressure spring 109. One end of the pressure spring 109 is disposed at the shoulder 103 and the other end is disposed at a cylindrical shoulder 111 of the coupling member 110. The coupling member 110 having a through-bore 114 in axial direction is configured with an inner recess 112 which is set off relative to the through-bore 114 and has at least one, preferably two or more diametrically opposing notch recesses 113 that are connected to recess 112. When moving the coupling member 110 against the restoring force of the pressure spring 109, at least one of the pins or cams 88 of control member 90 engages in the notch recesses 113, thereby bringing the coupling member 110 into fixed rotative engagement.

At the other end, the cylindrical body 101 has an opening (not referenced) corresponding to the interior space 102 and for partially inserting the coupling member 110. At the end that is oriented towards the endoscope 125, cylindrical body 101 is provided with at least one, preferably with two diametrically opposing recesses 108 extending through the wall of cylindrical body 101, and which are bounded by the stop collar 107 situated at the end of the cylindrical body.

As shown in a partial view in FIG. 7A, a connector 130 configured approximately in the shape of a housing is provided at the end of endoscope 125 facing the housing 100 respectively the coupling member 110. The connector 130 is provided with a first recess 131 which is corresponding to coupling member 110, and a second recess 132 which is adjacent thereto. At the inner circumferential surface of recess 131 a circular ring groove 131.1 is provided for engagement with a collar 115 integrally formed at the end facing the coupling member 110, such that the coupling member 110 forms a connection with the connector 130 of endoscope 125 by means of a bayonet catch or snap-lock.

Further shown in FIG. 7A is a cylindrical part 128 integrally formed at endoscope 125 and a first connection piece 126 which is integrally formed with cylindrical part 128 and for receiving the optical guide 140. The optical guide 140 projects through connection piece 126 and is coupled to line 18 which is operatively connected by means not shown here in detail, with the camera 19 (FIG. 1). The cylindrical part 128 of endoscope 125 has an interior space 127 oriented in axial direction. A tube-shaped working channel 133 is disposed within the interior space 127 with a guide tube 134 coaxially disposed therein; a surgical tool 135 is coaxially positioned within the guide tube 134. The guide tube 134 and the surgical tool 135 which is in the shape of an elongated wire are configured for flexibility.

At the proximal end of the wire-shaped surgical tool 135, a pressure piece 120 is attached thereto by means not shown here in detail. The surface of the pressure piece 120 facing in the direction of the guide tube 134 is configured as a circular face for abutment of the guide tube 134. At the opposite end, the pressure piece 120 is operatively connected to the control member 90 by means of a luer cone connector or a bayonet catch that is configured as coupling 85. In the embodiment as shown, the coupling 85 comprises a head piece 86 which is disposed at the control member 90. The head piece 86 is provided with a bore 87 forming a pocket hole and correspondingly configured for receiving a pin 121 which is disposed at the pressure piece 120.

The coupling connection of the pressure piece 120 to head piece 86 of control member 90, is preferably realized by means of the known luer cone connector or bayonet catch, whereby cams 123 disposed at pin 121 of pressure piece are received in a groove 89 provided in the pocket hole of bore 87 of the head piece 86. The locking effect is preferably enhanced by a pressure spring 122 supported at the pin 121 and disposed between the pressure piece 120 and the head piece of 86.

FIG. 7B is a top partial view of drive mechanism 145 showing the housing 100 with collar 107 and the cylindrical section piece 128 of endoscope 125, that is disposed by means of the connector 130 to the coupling member 110. There is furthermore shown the recess 108 disposed within the housing 100 and in a partially cut-away view, the coupling member 110 is shown with the notch recess 113 configured in a preferably flared shape for receiving each of the pins or cams 88 disposed at the control member 90.

FIG. 7C shows a first variation of a partial view of the drive mechanism 145.1 which is configured substantially identical to the drive mechanism 145 as described in association with FIG. 7A and which comprises the electric motor drive 95 with exit shaft 96, the drive shaft 93 operatively connected thereto, the housing 100 with cylindrical body 101 and the pressure spring 109 disposed interiorly therein. In a variation of the embodiment as depicted in FIG. 7A, the control member of drive mechanism 145.1 is configured as an actuator 90.1. At its front end, the actuator 90.1 is configured as a threaded spindle 94 and provided with a stop collar 99. The treaded spindle 94 is operatively connected to a thread (not referenced disposed at the rear wall 105. A switch 98 provided at the rear wall 105 for operative connection with the stop collar 99 of threaded spindle 94 is coupled to the control unit 97 for activating the electric motor drive mechanism 95.

Figure 8:
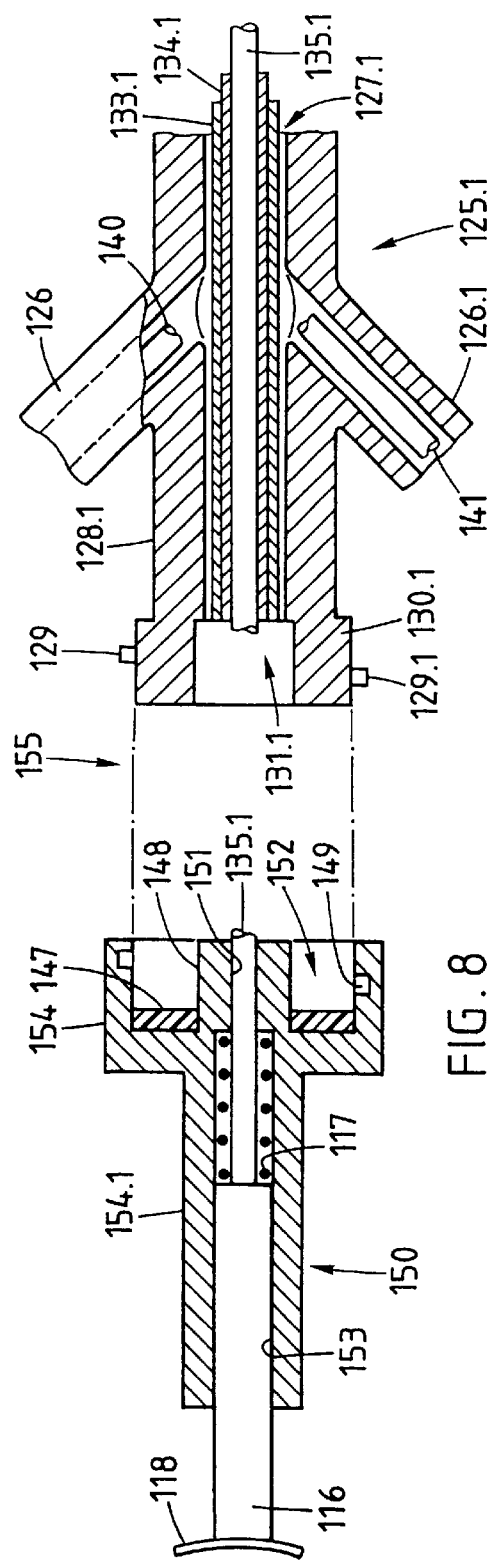
FIG. 8 is an exploded view of a section of a third embodiment of the drive mechanism for the surgical tool.

A further embodiment of a drive mechanism 155 is depicted in FIG. 8 shown as a sectional and partly exploded view. The drive mechanism 155 comprises a partially view of endoscope 125.1 and an adapter part 150. The parts 125.1 and 150 are described in detail in the following paragraphs.

The endoscope 125.1 shown in FIG. 8 has a cylindrical part 128.1, which is provided with a first connection piece 126 integrally formed with the cylindrical part 128.1, and set-off relative to the first connection piece is a second connection piece 126.1 exhibiting a tube-shaped channel 141 therein. The tube-shaped channel 141 extends through the second connection piece 126.1 and connects with the aspiration and irrigation unit 22 (FIG. 1) via line 21 in a manner not shown here in detail.

The cylindrical body 128.1 of endoscope 125.1 is provided with a co-axial interior space 127.1. The interior space 127.1 is configured for receiving elements 133.1 and 134.1 and 135.1 that are disposed co-axially inside each other as described in association with FIG. 7A. The guide tube 134.1 and the elongated surgical tool 135.1 are configured for flexibility. Further disposed at the endoscope 125.1 and set-off relative to the cylindrical body 128.1 is a connector part 130.1 that is provided with a recess 131.1 and which in fluid connection with the interior space thereof. Disposed at the outer circumference of the connector part 130.1 and set-off relative to each other are the snap-in cams 129 or like which upon insertion into adapter part 150 are brought into coupling engagement therewith.

The housing shaped adapter part 150 has a first cylindrical housing section 154 which is provided interiorly with a shoulder 148 and an elongated housing section 154.1 integrally formed thereon. Provided interiorly at the surface of the recess 152 of the first housing section 154 is, for example, a helical groove 149 and provided at the cylindrical shoulder 148 a seal 147. Through-bore passageways 153 and 151 set-off from each other, are axially extending inside the two housing sections 154 and 154.1. In the first through-bore passageway 153 a movable actuator 116 is biased against the restoring force of a pressure spring 117. At its proximal end, the actuator 116 is provided with pressure piece 118. At the distal end of the actuator 116, the surgical tool 135.1 configured as an elongated wire extends through the second through bore passageway 151 by means not shown here in detail.

The coupling connection of endoscope 125.1 with the adapter part 150 is preferably realized by means of the known luer cone connector or by means of the known bayonet closure, whereby the cams 129 or like provided at connector part 130.1 are brought into fixed rotative engagement with the groove 149 that are provided in recess 152 of housing section 154, and with the seal 147 a functional connection of the endoscope 125.1 with the adapter part 150 is realized.

The afore-described coupling connections of each of these elements are configured for example as a bayonet catch (snap closure). In a preferred embodiment, the afore-described elements are connected to each other by means of a locking cone connector whereby a coupling connection is realized. The known locking cone connections are provided with a 6% (luer) cone and are particularly suitable for hypodermics, cannulas and similar medical instruments. The specific configurations of such cone connections are described in more detail in the European Norm EN 1707.

Figure 9:
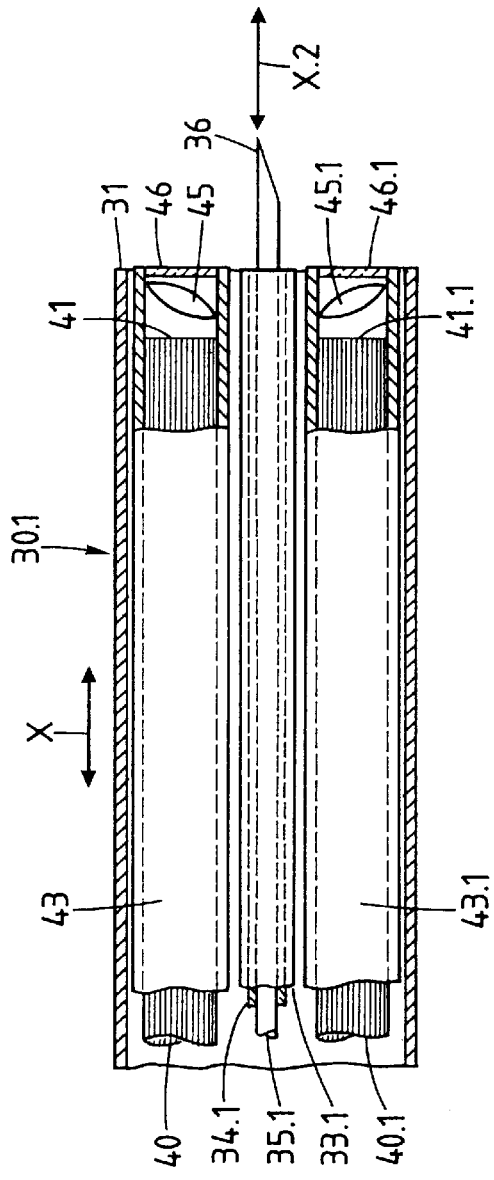
FIG. 9 is a sectional and partial top view of a probe configured as a hollow needle having two optical channels and a working channel arranged therebetween.

FIG. 9 shows a further embodiment of the probe 30.1 depicted in section on an enlarged scale with the two optical channel 43 and 43.1 disposed at a distance from each other and the optical guides 40 and 40.1 for transmission of stereo images (3-D) respectively disposed in each of the channels. Between each of the distal ends 41 and 41.1. of optical guides 40 and 40.1 and the distal ends of the tube-shaped optical channel 43 and 43.1, optical lenses 45 and 45.1 are respectively disposed within the interior space of the optical channels. The distal end of the tube-shaped optical channel 43 and 43.1 is preferably sealed by means of a transparent (translucent) disc 46 and 46.1 or like.

It should be noted here, that the optical guide 40 disposed in the optical channel 43 according to FIG. 3A and the two optical guides 40 and 40.1 disposed respectively in optical channels 43 and 43.1 according to FIG. 9 each are provided with optical elements suitably configured and disposed at the distal ends thereof. The embodiments as depicted in FIGS. 3A and 9, the optical element is respectively configured as an optical lens 45. The optical lens 45 is respectively disposed at the front face or the distal end of the each of the optical guides 40 or the distal end of each of the two optical guides 40 and 40.1

In a variation of this embodiment, not shown here in detail, each of the optical elements can be either integrated or ground—onto the distal end. The optical lens 45 disposed on the distal end or respectively the optical element that is integrated or ground-onto the front face of the optical guide 40 or 40 and 40.1 serves the function of focusing and precisioning the viewing field.

Furthermore, in the probe 30.1 between the two optical channels 43 and 43.1, a working channel 33.1 is provided and having the guide tube 34.1 co-axially disposed therein. The surgical tool is disposed in the guide tube 34.1. At the distal end of the surgical tool 35.1 the headpiece 36 which is configured as a working tool is integrally formed thereon and here, configured as a knife. The movements of each of the functional elements were described in connection with FIG. 3A.

It should be noted here, that the surgical tool 35 and 35.1 to 35.7 with the head piece 36 disposed thereon, can be activated by either manual means or by electric motor, and is thereby slidably movable relative to the distal end 31 of the probe 30 in axial direction and to a distance which is, for example, pre-set and adjustable and can therefore be locked into a focused and precisioned viewing position by means not depicted here in detail.

The functional elements of each of the drive mechanisms and the motions of the optical and mechanical elements resulting from the operative connection with the drive mechanism as well as their disposition relative to each other are not limited to the examples as set forth herein.

While the invention has been illustrated and described as embodied in a surgical tool for cutting the tissue of the trabecular meshwork, it is not intended to be limited to the details shown since various modifications and structural changes may be made without departing in any way from the spirit of the present invention.

What is claimed as new and desired to be protected by Letters Patent is set forth in the appended claims:

1. A device for microsurgically improving drainage of the aqueous humor via the trabecular meshwork into Schlemm's canal of the eye of a living being comprising:

an endoscope;
a tubular probe, having a proximal end operatively connected to the endoscope and adapted for insertion into the anterior chamber in the direction of the trabecular meshwork of the eye, wherein the probe has an optical channel and a working channel in axial relationship with the probe; and
an optical guide disposed in axial relationship with the optical channel for focusing and transmitting images from a viewing field;
a surgical tool, disposed in the working channel and movable at least in axial direction with respect to a distal end of the probe, for providing a passageway in the trabecular tissue to thereby connect the anterior chamber with the Schlemm's canal of the eye; wherein the surgical tool is operated by an electric motor coupled to a proximal end of the endoscope, said electric motor is disposed in a housing and is in operative connection by means of at least two catch members with an axially slidable sliding member disposed at the outer circumference of the housing for the manual adjusting movement of the surgical tool in axial direction of the probe; wherein the surgical tool is disposed on the electric motor with at a coupling member.

2. The device according to claim 1, wherein the optical guide is configured for transmitting a monoscopic visual representation of images from the viewing field.

3. The device according to claims 1, further comprising at least one optical element coaxially disposed within and at a distal end of the optical channel for focusing and precisioning the viewing field.

4. The device according to claim 3, wherein the optical guide at a distal end thereof is provided with at least one the optical element for focusing and precisioning the viewing field.

5. The device according to claim 4, wherein the optical element is an optical lens.

6. The device according to claim 5, wherein the optical lens is attached in the optical channel at a distance to the distal end of the optical guide.

7. The device according to claim 6, wherein the optical lens and the optical guide are configured for focusing on the viewing field in dependence on a distance of the surgical tool to a viewing position and which is adjustable in axial direction relative to a distal end of the probe.

8. The device according to claim 5, wherein the optical channel is sealed by a translucent disc and wherein the optical lens disposed in the optical channel is positioned between the distal end of the optical guide and the disc.

9. The device according to claim 3, wherein the optical guide has a front face at a distal end which is configured as lens-shaped optical element.

10. The device according to claim 1, further comprising a second tube-shaped optical channel co-axially disposed in the probe and at a distance from the one optical channel; and wherein the optical elements are disposed in each optical channel for focusing and precisioning the viewing field in dependence on a distance of the surgical tool which is adjustable in axial direction relative to a distal end of the probe.

11. The device according to claim 10, wherein the two optical channels with the optical elements disposed therein are configured for the stereoscopic transmission of images from the focused viewing field.

12. The device according to claim 10, further comprising a second optical guide and wherein each of the two optical channels are housing one optical guide configured at a distal end as a lens-shaped optical element for focusing and precisioning the viewing field.

13. The device according to claim 10, wherein at least one optical lens is disposed at the distal end of each of the optical guides attached in the optical channel for focusing and precisioning of the viewing field.

14. The device according to claim 1, further comprising a tube-shaped channel disposed in the probe in addition to the optical and working channels and extending in axial direction to the distal end of the probe and configured for receiving a light guide and adapted for lighting the focused viewing field.

15. The device according to claim 14, wherein the light guide is connected to a light source coupled to the endoscope.

16. The device according to claim 1, wherein the endoscope is connected to a camera for transmission of one of monoscopic or stereoscopic images from the viewing field that is focused by means of the optical elements; and wherein by means of a monitor screen connected to the camera the transmitted images of the viewing field can be visualized.

17. The device according to claim 1, wherein the surgical tool which is slidably movable in axial direction is adjustable at a predetermined advance into a fixed position.

18. The device according to claim 17, wherein the surgical tool is adjustable into a fixed position at a predetermined advance while focusing the viewing field.

19. The device according to claim 1, wherein the working channel which is stationary further comprises a guide tube co-axially disposed in the stationary working channel and in which the surgical tool is co-axially disposed; said guide tube is configured such that the surgical tool and the guide tube are slidably movable together or separately in axial direction relative to the distal end of the working channel.

20. The device according to claim 1, wherein the surgical tool is provided at the distal end with a head piece configured for microsurgery and together with the surgical tool is slidably movable in an axial direction and is rotatable about the longitudinal axis of the surgical tool for providing at least one of or both an oscillating and vibrating movement for surgical treatment of the trabecular meshwork.

21. The device according to claim 20, wherein the head piece of the surgical tool is configured as one of a one-edged or two-edged knife.

22. The device according to claim 20, wherein the distal head piece of the surgical tool is configured as one of a hollow cylindrical cannula or a drill.

23. The device according to claim 22, wherein the hollow cylindrical cannula is configured at a front face as one of a saw-toothed router or a cutting edge.

24. The device according to claim 20, wherein the head piece of the surgical tool is either configured in a shape selected from the group consisting of a forceps, a clamping element and a scissors for cuttingly and clampingly bringing into engagement with the tissue of the trabecular meshwork by means of the surgical tool which is axially movable relative to the guide tube.

25. The device according to claim 1, and further comprising another working channel co-axially disposed within the probe and extending to the distal end of the probe and which is connected to an aspiration and irrigation unit coupled to the endoscope by means of a coupling line.

26. The device according to claim 1, wherein the optical channel and the working channel disposed in the probe are each in the shape of a tube.

27. The device according to claim 26, wherein the probe has one of an elliptical-shaped or an oval-shaped cross section with an outer width (B) of about 2.4 mm and an outer height (H) of about 1.25 mm.

28. The device according to claim 1, wherein the electric motor drive is provided with means for moving the surgical tool in at least one of an axial movement and a rotational movement within the probe.

29. The device according to claim 1, wherein the means for driving the surgical tool is an electric motor drive and wherein the surgical tool has a proximal end which is in operative connection via a coupling with a drive shaft of the electric motor for rotational movement about a longitudinal axis and for a manually driven axially slidable adjusting movement.

30. The device according to claim 1, wherein the endoscope is configured in two or more parts that are coupled to each other by means of bayonet closures.

31. The device according to claim 1, wherein the endoscope is configured in two or more parts coupled to each other by means of a locking cone connector.

32. The device according to claim 1, wherein the surgical tool is co-axially disposed in a guide tube which is configured as a flexible guide tube for insertion into the working channel of the probe.

33. The device according to claim 1, wherein the endoscope is coupled to one end of a coupling member and another end of the coupling member is slidably movable in the housing and against the restoring force of a spring, and wherein a control member is axially disposed in the coupling member and the housing, said control member is in operative connection at one end with the surgical tool via a coupling and at an opposite end with the electric motor via the drive shaft.

34. The device according to claim 33, wherein the surgical tool is at the proximal end thereof operatively connected by means of the coupling to a drive control member which is drivable by the electric motor for rotational movement about the longitudinal axis and for the manual adjustment movement in axial direction.

35. The device according to claim 34, wherein the control member disposed in the housing is configured at a proximal end as a threaded spindle, which is axially slidable as a result of the rotation of the drive shaft.

36. The device according to claim 35, wherein the axial movement of the control member can be actuated by a switch disposed at the housing and connected to a control unit.

37. The device according to claim 1, further comprising a drive mechanism for coupling to a proximal end of the endoscope and which is manually controllable for the axial adjusting movements and the rotational movement about the longitudinal axis of the surgical tool.

38. The device according to claim 37, further comprising an adapter part for coupling engagement with the proximal end of the endoscope and configured as a housing and has at one end a housing section integrally formed thereon, and is provided at another end with an elongated hollow cylindrical housing section with an actuator disposed therein which is slidably movable against the restoring force of a pressure spring.

39. The device according to claim 37, wherein the surgical tool is disposed within the endoscope and operatively connected to an actuator at the proximal end of the surgical tool, said tool is movable about the rotational axis by means of manual operation of the actuator and against the restoring force of the pressure spring for the axial adjusting movement of the surgical tool.

* * * * *